United States Patent

Jarreau et al.

Patent Number: 5,264,443
Date of Patent: Nov. 23, 1993

[54] 3-ARYL OXAZOLIDINONE COMPOUNDS AND THERAPEUTIC USE THEREOF

[75] Inventors: Francois Jarreau, Versailles; Jean-Jacques Koenig, Maisons Laffitte; Vincenzo Rovei, Rueil Malmaison, all of France

[73] Assignee: Delalande S.A., France

[21] Appl. No.: 865,885

[22] Filed: Apr. 9, 1992

[30] Foreign Application Priority Data

Apr. 16, 1991 [FR] France ............... 91 04641

[51] Int. Cl.$^5$ ............... C07D 213/30; A61K 31/42
[52] U.S. Cl. ............... 514/340; 546/275
[58] Field of Search ............... 546/275; 514/340

[56] References Cited

U.S. PATENT DOCUMENTS

| | | | |
|---|---|---|---|
| 2,954,381 | 9/1960 | Shapiro | 546/275 |
| 3,290,326 | 12/1966 | Hoffer | 546/275 |
| 4,133,675 | 1/1979 | Schurter et al. | 546/275 |
| 4,435,415 | 3/1984 | Bourgery et al. | 546/275 |

Primary Examiner—C. Warren Ivy
Assistant Examiner—Zinna N. Davis
Attorney, Agent, or Firm—Finnegan, Henderson, Farabow, Garrett & Dunner

[57] ABSTRACT

Derivatives having the formula:

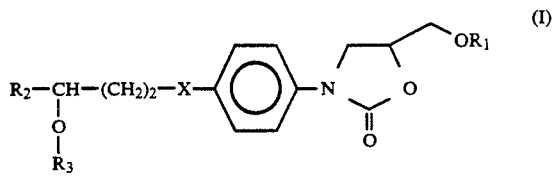

where $R_1$ denotes $C_1$–$C_4$ alkyl; X denotes oxygen or methylene; $R_2$ denotes $C_1$–$C_4$ alkyl or $CF_3$; $R_3$ denotes a $CH_2R_4$ group in which $R_4$ is (i) a pentagonal or hexagonal aromatic heterocyclic group comprising one or two nitrogen atoms and optionally fused with a benzene ring or (ii) a group having the formula

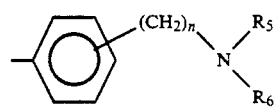

where n=0 or 1, and $R_5$ and $R_6$ independently denote $C_1$–$C_4$ alkyl or benzyl, and $R_5$ and $R_6$ also, together with the nitrogen atom to which they are bonded, form a piperidino or pyrrolidino or morpholino or N-methyl piperazino radical, and their N-oxide forms and acid addition salts of these derivatives and their N-oxide forms, the derivatives being in various stereoisomeric forms or in the form of a mixture of these forms, including the racemic form.

15 Claims, No Drawings

3-ARYL OXAZOLIDINONE COMPOUNDS AND THERAPEUTIC USE THEREOF

The invention relates to novel derivatives of 3-aryl 2-oxazolidinone, a method of preparing them and use thereof in therapy.

More specifically the derivatives have the formula:

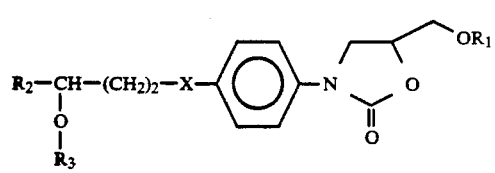

where:

$R_1$ represents $C_1$-$C_4$ alkyl;

X represents an oxygen atom or a methylene group;

$R_2$ represents $C_1$-$C_4$ alkyl or $CF_3$;

$R_3$ represents a $CH_2R_4$ group in which $R_4$ is (i) a pentagonal or hexagonal aromatic heterocyclic group comprising one or two nitrogen atoms, (ii) a pentagonal or hexagonal aromatic heterocyclic group comprising one or two nitrogen atoms and fused with a benzene ring, or (iii) a group having the formula:

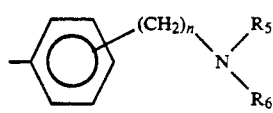

where:

n=0 or 1 and $R_5$ and $R_6$ independently denote $C_1$-$C_4$ alkyl or benzyl, and also $R_5$ and $R_6$ together with the nitrogen atom to which they are bonded can form a piperidino, pyrrolidino, morpholino or N-methyl piperazino radical.

Note that the derivatives (I) have two asymmetrical carbon atoms. They can therefore exist in different stereoisomeric forms or in the form of a mixture of these forms, including the racemic form. The invention therefore covers the various forms as thus defined.

The invention includes the N-oxides of the N-oxidisable derivatives (I), and the acid addition salts of the derivatives (I) and their N-oxide. These salts can be formed with inorganic acids such as hydrochloric or sulphuric or phosphoric acid or with organic acids such as fumaric, maleic, succinic, oxalic, citric or tartaric acid.

The following are particular examples of $R_4$ groups: imidazolyl, pyrazolyl, pyridyl, pyrimidinyl, pyrazinyl, pyridazinyl, quinolyl, isoquinolyl, quinoxalinyl, quinazolinyl and cinnolinyl.

Preference is given to:

derivatives (I) in which $R_4$=imidazolyl, derivatives (I) in which $R_4$=pyridyl, derivatives (I) in which $R_4$=quinolyl, derivatives (I) in which $R_4$=pyridyl N-oxide, and derivatives (I) in which $R_4$=quinolyl N-oxide.

The following are particular examples of the derivatives (I):

a) those in which $R_1$=$C_1$-$C_4$ alkyl, X denotes oxygen, $R_2$=$CF_3$ and $R_4$=pyridyl;

b) those in which $R_1$=$C_1$-$C_4$ alkyl, X denotes oxygen, $R_2$=$CF_3$ and $R_4$=pyridyl N-oxide;

c) those in which $R_1$=$C_1$-$C_4$ alkyl, X denotes oxygen, $R_2$=$CF_3$ and $R_4$=pyridyl, and the asymmetrical carbon in the oxazolidinone ring has the configuration (R);

d) those in which $R_1$=$C_1$-$C_4$ alkyl, X denotes oxygen, $R_2$=$CF_3$ and $R_4$=pyridyl N-oxide, and the asymmetrical carbon in the oxazolidinone ring has the configuration (R);

e) those in which $R_1$=$C_1$-$C_4$ alkyl, X denotes oxygen, $R_2$=$CF_3$ and $R_4$=pyridyl and the asymmetrical carbon $R_2$—$C^*H(OR_3)$— has the configuration (R);

f) those in which $R_1$=$C_1$-$C_4$ alkyl, X denotes oxygen, $R_4$=pyridyl N-oxide and the asymmetrical carbon $R_2$—$C^*H(OR_3)$— has the configuration (R);

g) those in which $R_1$=$C_1$-$C_4$ alkyl, X denotes oxygen, $R_2$=$CF_3$, $R_4$=pyridyl and the asymmetrical carbon $R_2$—$C^*H(OR_3)$— has the configuration (S);

h) those in which $R_1$=$C_1$-$C_4$ alkyl, X denotes oxygen, $R_4$=pyridyl N-oxide and the asymmetrical carbon $R_2$—$C^*H(OR_3)$— has the configuration (S);

i) those in which $R_1$=$C_1$-$C_4$ alkyl, X denotes oxygen, $R_2$=$CF_3$, $R_4$=pyridyl and the configuration is (R, R);

j) those in which $R_1$=$C_1$-$C_4$ alkyl, X denotes oxygen, $R_2$=$CF_3$, $R_4$=pyridyl N-oxide and the configuration is (R, R);

k) derivatives as per a) to j) where X represents a $CH_2$ group instead of oxygen; and l) derivatives as per a) to k) in the form of acid addition salts.

The invention also relates to methods of preparing the derivatives (I) and their N-oxide if any, the methods being in accordance with diagrams 1 to 4 hereinafter, in which the symbols $R_1$, X, $R_2$ and $R_3$ have the same meaning as in formula (I).

DIAGRAM 1

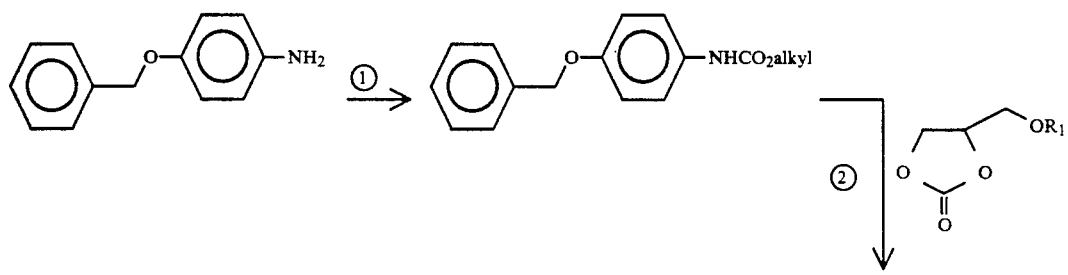

-continued
DIAGRAM 1
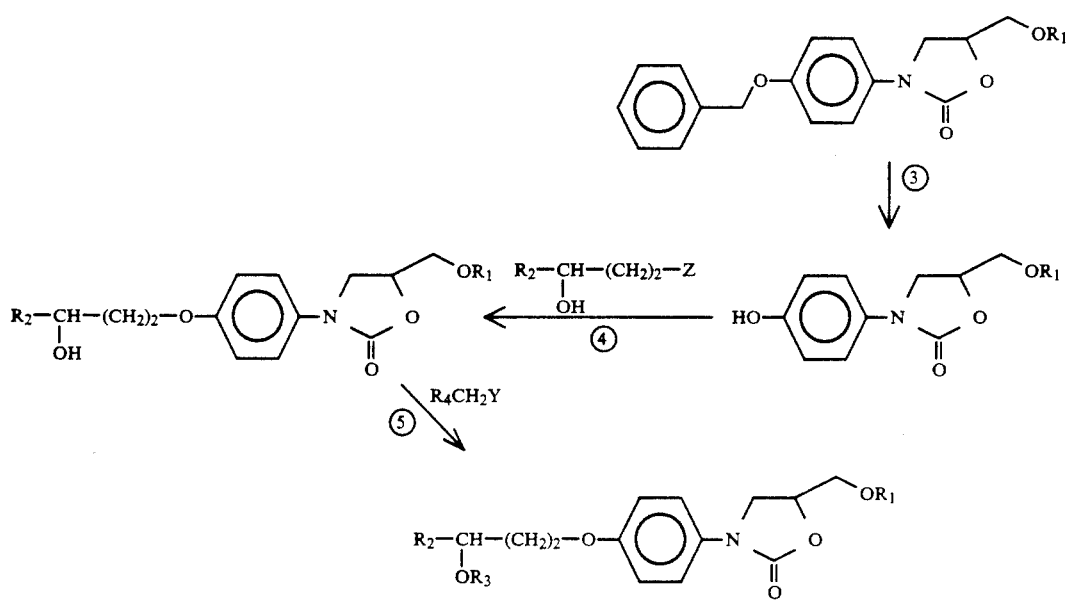
Z = OTs, OMs or halogen
Y = halogen
DIAGRAM 2
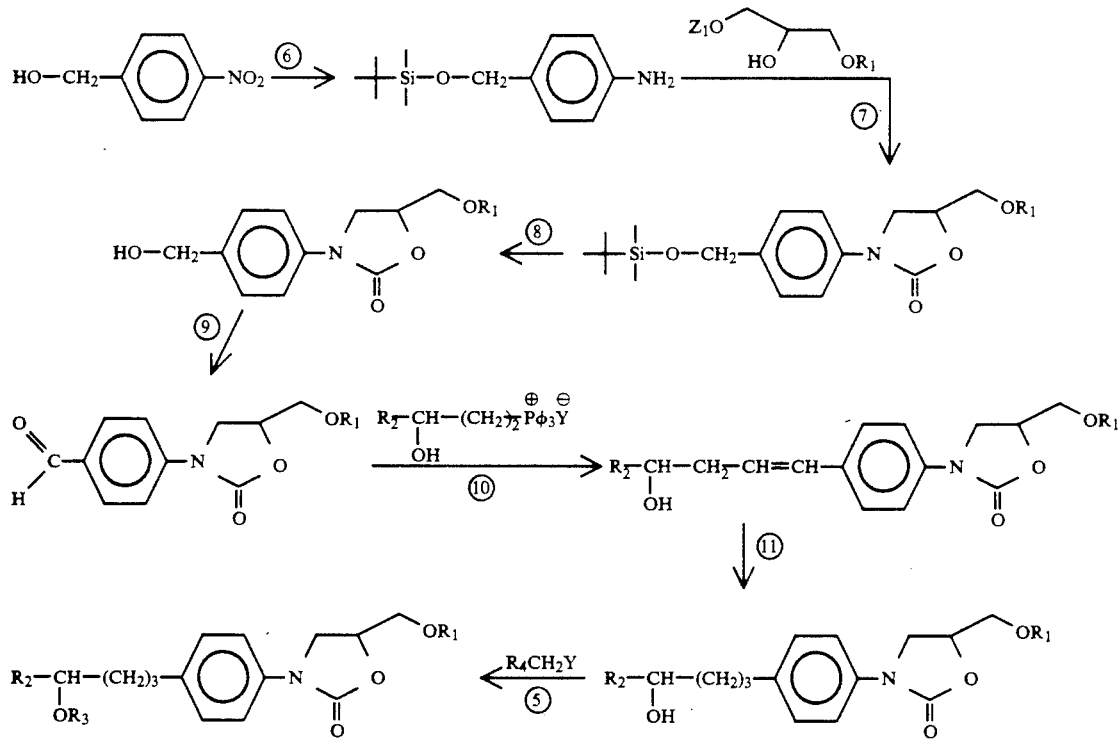
$Z_1$ = Ts or Ms
Y = halogen

DIAGRAM 3

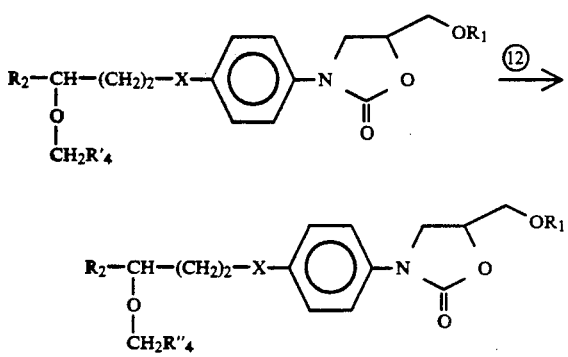

R'$_4$ = chosen from among the N-oxidisable groups
R''$_4$ = R'$_4$N-oxide

DIAGRAM 4

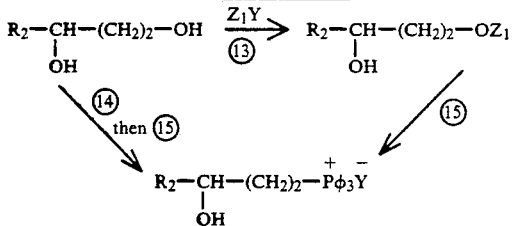

Z$_1$ = Ts or Ms
Y = halogen

The indices (1) to (15) appearing in the aforementioned diagrams have the following meanings:

(1) Condensation with an alkyl chloroformate, e.g. ethyl chloroformate, in the presence of a base, inter alia NaHCO$_3$, in a solvent water and THF mixture at ambient temperature.

(2) Condensation when hot (towards 150° C.) in the presence of a base such as K$_2$CO$_3$, the reaction maintaining the stereochemistry; or Condensation in toluene in the presence of LiBr and nBu$_3$PO.

(3) Debenzylation in an alcoholic solvent such as methanol or ethanol in the presence of hydrogen and a catalyst, inter alia 10% palladium on carbon, moistened or not.

(4) O. alkylation in an anhydrous aprotic solvent such as methyl ethyl ketone or DMF in the presence of a base, inter alia K$_2$CO$_3$, or O. alkylation in an aprotic organic solvent such as DMF and/or THF and in the presence of an alkali metal hydride such as sodium hydride.

(5) O. alkylation, inter alia under phase transfer conditions in the presence of a catalyst such as a quaternary ammonium bromide, e.g. tertiobutyl ammonium bromide, in a toluene/50% aqueous NaOH mixture at ambient temperature or when hot.

(6) O. silylation of alcohol in an aprotic organic solvent such as THF in the presence of a base, inter alia imidazole, and terbutyl dimethyl chlorosilane; then reduction of the nitrated derivative with iron filings in the presence of ammonium chloride.

(7) Condensation in the presence of phosgene and a base, inter alia dimethyl aniline or diethyl aniline in an organic solvent such as methylene chloride or dichloroethane; then cyclisation by heating in an organic, inter alia alcoholic, solvent such as ethanol in the presence of a base, inter alia potash.

(8) Hydrolysis in an organic solvent, inter alia THF, in the presence of a quaternary ammonium compound, inter alia tetrabutyl ammonium fluoride.

(9) Oxidation in the presence of an oxalyl chloride, DMSO and a base, inter alia triethylamine, in an aprotic organic solvent such as methylene chloride.

(10) Condensation in the presence of a base, inter alia K$_2$CO$_3$, and formamide in an aprotic solvent, inter alia dioxan, preferably with reflux, or condensation in the presence of LDA (lithium diisopropylamide) in a mixture of solvents, inter alia DMSO/THF.

(11) Hydrogenation at atmospheric pressure of hydrogen in an organic solvent, inter alia ethyl acetate, in the presence of a catalyst such as 10% palladium on carbon, moistened or not, or PtO$_2$, or hydrogenation under pressure of hydrogen, inter alia at 5 atmospheres, in the presence of 10% palladium on carbon, moistened or not, or PtO$_2$, in an alcoholic solvent, inter alia ethanol.

(12) N-oxidation, e.g. by metachloroperbenzoic acid, inter alia in an aprotic solvent such as methylene chloride at ambient temperature.

(13) Condensation in an organic solvent, inter alia pyridine, THF or CH$_2$Cl$_2$ and a base, inter alia 4-dimethylamino pyridine or Et$_3$N.

(14) As per Can. J. Chem. 1968, 46, 86.

(15) As per Helv. Chim. Acta 59, 755 (1976).

Note that the various stereoisomeric forms of the compounds according to the invention can be separated by conventional methods, e.g. the method of forming a salt with a chiral acid, or a given isomer can be prepared from chiral reagents.

The following preparations are given by way of example to illustrate the invention:

EXAMPLE 1

3-(4-benzyloxyphenyl)5-methoxymethyl(R)2-oxazolidinone (MD 200404)

Stage 1: 2,2-dimethyl4-methoxymethyl(S)dioxolane (Code No. MD 370486)

910 g of NaOH in pellets was added to 910 ml water, followed at ambient temperature by 5 l methylene chloride, 44.4 g (0.195 mol) benzyl triethyl ammonium chloride, 8558.6 g (6.5 mols) of 2,2-dimethyl 4-hydroxymethyl(S)dioxolane and 1229.5 g (9.75 mols) of dimethyl sulphate. The reaction medium was agitated for 12 hours and poured on to water. The organic phase was concentrated. The expected compound was obtained by distillation.

B.P.: 45° C. at 10 mm Hg;

$[\alpha]^{20}_D$: +7.9° (C=4, CH$_3$OH)

IR (microcell) $\nu$ cm$^{-1}$: 2995, 2940, 2820, 1380, 1370, 840;

NMR$^1$H (CDCl$_3$) $\delta$ ppm: 1.2 (3H); 1,4 (3H); 3.35 (3H); 3.4-4.4 (3H); 4 (2H).

Stage 2: 3-methoxy propane 1,2-diol (R) (Code Number MD 370487)

A solution of 950.3 g (6.5 mols) of MD 370486 was heated in 4510 ml water at 60° C. and 3.2 ml of concentrated hydrochloric acid was added. Next, 9 ml of triethylamine was added and the reaction medium was concentrated and distilled. The expected compound was obtained with an 84% yield.

B.P.: 66° C. at 1 mm Hg;

$[\alpha]^{20}_D$: −6.4° (C=4, CH$_3$OH)

IR (microcell) $\nu$ cm$^{-1}$: 3300, 3500, 2960, 2945, 2910;

NMR$^1$H(DMSOd6) $\delta$ ppm 3.2–3.7 (8H); 4.5 (2H exch.).

Stage 3: 4-methoxymethyl 1,3-dioxolan 2-one(S) (Code No. MD 360 287).

A mixture of 14 g (0.132 mol) of 3-methoxy propane 1,2-diol (R) and 31.16 g (0.264 mol) of diethyl carbonate was heated in the presence of 0.108 g of 50% sodium hydride until the alcohol formed had distilled. When the reaction was complete, the expected product was distilled.

B.P. 0.3=117° C.;

Yield: 93%;

$[\alpha]^{20}_D$: −32.2° (C=1, CH$_2$Cl$_2$);

IR (microcell) $\nu$ CO: 1790 cm$^{-1}$

NMR$^1$H (CDCl$_3$) $\delta$ ppm: 3.4 (3H); 3.6 (2H); 4.3–4.9 (3H).

Stage 4: N-ethoxycarbonyl 4-benzyloxy aniline (Code No: MD 360343)

6.3 g sodium bicarbonate followed by 5.28 ml (55.10$^{-3}$ mol) of ethyl chloroformate was added to a solution of 10 g (10$^{-3}$ mol) of 4-benzyloxy aniline in 90 ml THF and 10 ml water. After agitation for 18 hours, the reaction medium was filtered and concentrated. The residue was dissolved in ethyl acetate. The organic solution was washed with water, dried on Na$_2$SO$_4$ and concentrated. The product was obtained with a 91% yield.

M.P.=98° C.;

IR (microcell) $\nu$ cm$^{-1}$: 3320, 1700, 1510–1530, 1230

NMR$^1$H (CDCl$_3$) $\delta$ ppm: 1.2 (3H); 4.2 (2H); 5 (2H); 6.7 (1H); 6.9 (2H); 7.2 (2H).

Stage 5: 3-(4-benzyloxyphenyl)5-methoxymethyl(R)2-oxazolidinone (Code No: MD 200404)

1 g (3.6×10$^{-3}$ mol) of MD 360343, 0.099 g (0.72×10$^{-3}$ mol) of K$_2$CO$_3$ and 0.586 g (4.5×10$^{-3}$ mol) of MD 360287 (obtained in stage 3) were heated at 160° C. for 3 hours. After cooling, the reaction medium was dissolved in methylene chloride, washed with water, dried on Na$_2$SO$_4$ and concentrated. The product was recrystallised from isopropanol.

Yield=71%

M.P.=101° C.

$[\alpha]^{20}_D$: −41.5° (C=1, CH$_2$Cl$_2$).

The following were obtained by an identical procedure but starting from the appropriate reagents:

3-(4-benzyloxyphenyl)5-methoxymethyl(S)2-oxazolidinone (Code No. MD 340190)

M.P.=101° C.; $[\alpha]^{20}_D$: +41.9° (C=1, CH$_2$Cl$_2$), and 3-(4-benzyloxyphenyl)5-ethoxymethyl(R)2-oxazolidinone (Code No. MD 230 242)

M.P.=78° C.; $[\alpha]^{20}_D$: −35.9° (C=1, CH$_2$Cl$_2$); IR (KBr) $\nu$cm$^{-1}$: 1750, 1735.

EXAMPLE 2

3-(4-hydroxy phenyl)5-methoxymethyl(R)2-oxazolidinone (Code No. MD 200405)

A stream of hydrogen at normal pressure was conveyed through a solution of 13 g (0.047 mol) of compound MD 200404 in 80 ml ethanol and 40 ml CH$_2$Cl$_2$ in the presence of 2.6 g of 10% Pd/C 50% moistened.

When the reaction was complete, the solution was filtered and concentrated. The expected product was obtained with a 100% yield.

M.P.=112° C. $[\alpha]^{20}_D$: −67° (C=1, CH$_3$OH); IR (KBr) $\nu$cm$^{-1}$: 3260, 1730.

The following were obtained by an identical procedure but starting from the corresponding reagents:

3-(4-hydroxyphenyl)5-methoxymethyl(S)2-oxazolidinone (Code No. MD 200717)

M.P.=114° C.; $[\alpha]^{20}_D$: +66° (C=1, CH$_3$OH), and 3-(4-hydroxyphenyl)5-ethoxymethyl(R)2-oxazolidinone (Code No. MD 230 243)

M.P.=92° C.; $[\alpha]^{20}_D$: −58.9° (C=1, CH$_3$OH); IR (KBr) $\nu$cm$^{-1}$: 3300, 1770

EXAMPLE 3

3-[4-(4,4,4-trifluoro 3-hydroxy(R)butoxy) phenyl]5-methoxymethyl(R)2-oxazolidinone (Code No. MD 370503)

Stage 1: 4,4,4-trifluoro 1-tosyloxy 3-butanol(R) (Code No. MD 230099)

0.12 g of 4-dimethylamino pyridine and a solution of 198.4 g (1.041 mol) of tosyl chloride in 200 ml CH$_2$Cl$_2$) were added to a solution of 120 g (0.833 mol) of 4,4,4-trifluoro 1,3-butanediol(R) (C.A. 111, 31747 p) in 335 ml pyridine. After agitation for 1 hour and 20 minutes, 1.2 l of CH$_2$Cl$_2$ and 1.5 l water were added. The organic phase was concentrated and the product was purified by chromatography [silica; eluent: heptane (80)/ethyl acetate (20)] and was obtained with a 78% yield. It was used directly for the next step.

Stage 2: 3-[4-(4,4,4-trifluoro 3-hydroxy(R)butoxy)-phenyl]5-methoxymethyl(R)2-oxazolidinone (Code No. MD 370503)

161.5 g K$_2$CO$_3$ was added to a solution of 192.1 g (0.644 mol) of compound MD 200405 (Example 2) in 400 ml DMF and reflux-heated, followed by suspension of the compound MD 230099 in 200 ml DMF. After 1 hour, the reaction medium was cooled and 1.2 l toluene per liter of water was added.

After extraction of the aqueous phase with toluene, the organic phases were concentrated to dryness. The product was recrystallised from a mixture of ethanol and isopropyl ether.

Yield=60.8% M.P.=101° C.;

NMR$^1$H (CDCl$_3$) $\delta$ ppm: 2.05 (2H); 3.4 (3H): 3.6 (2H); 3.6–4.4 (6H, of which 1 exchangeable); 4.6 (1H); 6.8 (2H); 7.3 (2H).

NMR$^{13}$C (DMSO$^d$6): Cq: 154.6; 154.4; 125.9 ($^1$JCF: 289.6 Hz); 131.8; CH: 119.8; 114.8; 71.3; 65.4 ($^2$JCF: 30.4 Hz); CH$_2$: 72.5; 63.2; 46.6; 29.4; CH$_3$: 58.7.

IR (KBr) $\nu$cm$^{-1}$: 3400, 1730, 1720; $[\alpha]^{20}_D$: −11.5° (C=1, CH$_2$Cl$_2$).

3-[4-(4,4,4-trifluoro 3-hydroxy(S)butoxy)phenyl]5-methoxymethyl(R)2-oxazolidinone (Code No. MD 370504) was obtained in the same manner but starting from 4,4,4-trifluoro 1-tosyloxy 3-butanol(S) and compound MD 200405:

M.P.=121° C.; $[\alpha]^{20}_D$: −59.7° (C=1, CH$_2$Cl$_2$);

NMR$^1$H (CDCl$_3$) $\delta$ ppm: 2.1 (2H); 3.4 (4H of which 1 exch.); 3.6 (2H); 3.7–4.4 (5H); 4.7 (1H); 6.8 (2H); 7.4 (2H);

IR (KBr) $\nu$cm$^{-1}$: 3420, 1735.

The mixture of diastereoisomers 3-[4-(4,4,4-trifluoro 3-hydroxybutoxy)phenyl]5-methoxymethyl(R)2-oxazolidinone (Code No. 230016) was obtained under the same conditions, starting from the racemic compound 4,4,4-trifluoro 1-tosyloxy 3-butanol (Code No. MD 370272) and the compound MD 200405.

NMR¹H (CDCl₃+DMSO) δ ppm: 1.8-2.3 (2H); 3.4 (3H); 3.6 (2H); 3.8-4.4 (5H); 4.7 (1H); 5.3 (1H exchangeable); 6.9 (2H); 7.4 (2H);

IR (KBr) νcm⁻¹: 3400, 1755, 1735; M.P.=103° C.; $[\alpha]^{20}_D$: −35,2° (C=1, CH₂Cl₂). The following were obtained similarly but starting from the corresponding substances:

3-[4-(4,4-trifluoro 3-hydroxy(S)butoxy)phenyl]5-methoxymethyl(S)2-oxazolidinone (Code No. 230154)
$[\alpha]^{20}_D$: +9.9° (C=1,CH₂Cl₂); M.P.=100° C.;

3-[4-(4,4-trifluoro 3-hydroxy(R)butoxy)phenyl]5-methoxymethyl(S)2-oxazolidinone (Code No. 230151)
$[\alpha]^{20}_D$: +59.2° (C=1,CH₂Cl₂); M.P.=123° C.;

3-[4-(4,4-trifluoro 3-hydroxy(R)butoxy)phenyl]5-ethoxymethyl(R)2-oxazolidinone (Code No. 230197)
M.P.=91° C.; $[\alpha]^{20}_D$: −11.4° (C=1, CH₃OH); IR (KBr) νcm⁻¹: 3400, 1750, 1735;

NMR¹H (CDCl₃) δ ppm: 1.1 (3H); 3.3-4.4 (9H); 4.7 (1H); 6.3 (1H exch); 6.9 (2H); 7.4 (2H);

3-[4-(3-hydroxy(R)butoxy)phenyl]5-methoxymethyl(R)2-oxazolidinone (Code No. MD 370120)
M.P.=76° C.; $[\alpha]^{20}_D$: −50.7° (C=1, CH₂Cl₂);

3-[4-(3-hydroxy(R)butoxy)phenyl]5-methoxymethyl(S)2-oxazolidinone (Code No. MD 370123)
M.P.=44° C.; $[\alpha]^{20}_D$: +33° (C=1, CH₂Cl₂);

3-[4-(3-hydroxy(S)butoxy)phenyl]5-methoxymethyl(S)2-oxazolidinone (Code No. MD 370121)
M.P.=76° C.; $[\alpha]^{20}_D$: +50.4° (C=1, CH₂Cl₂);

3-[4-(3-hydroxy(S)butoxy)phenyl]5-methoxymethyl(R)2-oxazolidinone (Code No. MD 370122)
$[\alpha]^{20}_D$: −33.4° (C=1, CH₂Cl₂);

NMR¹H (CDC¹₃) δ ppm: 1.2 (3H); 1.8 (2H); 2.2 (1H exch); 3.4 (3H); 3.6 (2H); 3.7-4.2 (5H); 4.7 (1H); 6.8 (2H); 7.4 (2H);

NMR¹H (CDCl₃) δ ppm: Cq: 155.6; 154.9; 131.6; CH: 120.2; 115; 71.3; 65.6; CH₂: 72.7; 65.9; 47.6; 38.2; CH₃: 59.6; 23.6;

IR (KBr) ν cm⁻¹: 3380-3400, 1730, 1755;
M.P.==49° C.;

3-[4-(3-hydroxybutoxy)phenyl]5-methoxymethyl(R)2-oxazolidinone (Code No. MD 370284)
NMR¹H (CDCl₃) δ ppm: 1.2 (3H); 1.8 (2H); 2.6 (1H exch); 3.4 (3H); 3.6 (2H); 3.7-4.2 (5H); 4.7 (1H); 6.8 (2H); 7.4 (2H);

IR (KBr) ν cm⁻¹: 3400, 1745, 1730;
$[\alpha]^{20}_D$: −41.5° (C=1, CH₂Cl₂)

EXAMPLE 4

Racemic mixture of diastereoisomers of 3-[4-(3-hydroxybutoxy)phenyl]5-methoxymethyl 2-oxazolidinone (Code No MD 370047)

28.2 g (0.2 mol) of K₂CO₃ and 22.8 g (0.102 mol) of 3-(4-hydroxyphenyl) 5-methoxymethyl 2-oxazolidinone (Code No. 780232) were added to a solution of 27.5 g (0.112 mol) of 1-tosyloxy 3-butanol in 250 ml of methyl ethyl ketone. The mixture was reflux-heated for 4½ hours. After filtration and concentration, the residue was dissolved in 200 ml CH₂Cl₂ and the organic phase was washed with water saturated with NaCl, dried over Na₂SO₄ and concentrated. After purification by chromatographic flash [silica, eluent: CH₂Cl₂ (98)/CH₃OH(2)], the expected product was obtained with a 70% yield:
M.P. =58° C.;

NMR¹H (CDCl₃) δ ppm: 1.2 (3H); 1.8 (2H); 2.5 (1H exch); 3.4 (3H); 3.6 (2H); 3.7-4.2 (5H); 4.7 (1H); 6.8 (2H); 7.4 (2H);

IR (KBr) ν cm⁻¹: 3400, 1750, 1730.

The racemic mixture of diastereoisomers 3-[4-(4,4,4-trifluoro 3-hydroxybutoxy)phenyl]5-methoxymethyl 2oxazolidinone (Code No MD 370167) was obtained in the same manner but starting from 4,4,4-trifluoro 1-tosyloxy 3-butanol and 3-(4-hydroxyphenyl)5-methoxymethyl 2-oxazolidinone (Code No. MD 780232).
M.P.=89° C.;.

NMR¹H (CDCl₃) δ ppm: 2.05 (2H); 3.4 (3H); 3.5 (1H exch); 3.6 (2H); 3.7-4.3 (5H); 4.7 (1H): 6.8 (2H), 7.3 (2H);

IR (KBr) ν cm⁻¹: 3400, 1750, 1785.

EXAMPLE 5

3-[4-(4-hydroxy(R)pentyl)phenyl]5-methoxymethyl(R)2-oxazolidinone (Code No. MD 230238)

Stage 1: 4-Terbutyl dimethyl silyloxy methyl 1-nitro benzene (Code No MD 230245)

310 g (4.559 mols) of imidazole followed by 504 g (3.347 mols) of terbutyl dimethyl chlorosilane were added to a solution of 465.4 g (3.039 mols) of paranitrobenzyl alcohol in 2.5 l of DMF. After agitation for one hour at ambient temperature, the reaction medium was poured on to water. The aqueous phase was extracted with methylene chloride. The organic phase was dried on Na₂SO₄ and concentrated, yielding an oil which corresponded to the expected compound.

NMR¹H (CDCl₃) δ ppm: 0.2 (6H); 1 (9H); 4.9 (2H); 7.6 (2H); 8.2 (2H);

IR (microcell) ν cm⁻¹: 1520, 1340, 1030, 840.

Stage 2: 4-Terbutyl dimethylsilyloxy methyl aniline (Code No MD 230246)

77.2 g (0.288 mol) of the preceding compound MD 230245 and 120.9 g of iron filings were added to 772 ml of 0.1 N ammonium chloride and reflux-heated for 2 hours. After cooling, 20 ml of concentrated ammonia were added, and the reaction medium was filtered and extracted with toluene. The organic phase was washed with water, dried on Na₂SO₄ and concentrated, yielding the expected compound:

B.P. 0.01 mm Hg: 88°-93° C.;

NMR¹H (CDCl₃) δ ppm: 0.2 (6H); 1.05 (9H); 3.6 (2H); 4.8 (2H); 6.75 (2H); 7.2 (2H);

IR (microcell) ν cm⁻¹: 3450, 3350

Stage 3: 3-methoxy propane 1,2-diol tosylate(S) (Code No. MD 370488).

A solution of 371.4 g (3.5 mols) of MD 370487 in 100 ml toluene was cooled to 13° C. and 565 ml of pyridine were added, followed gradually by a solution of 700.6 g (3.675 mols) of paratoluene sulphonyl chloride in 775 ml toluene.

The reaction medium was agitated for 12 hours and poured on to water. The organic phase was washed with 2N hydrochloric acid and concentrated. The expected product was obtained with a 58% yield after chromatography [silica, eluent: CH₂Cl₂ (50)/petroleum ether (50)];

$[\alpha]^{20}_D$: +5.3° (C=4, CH₃OH);

IR(microcell) ν cm⁻¹: 3500, 1335, 1185, 1170

NMR¹H (CDCl₃) δ ppm: 2.4 (3H); 3.1 (1H exch); 3.2-3.6 (5H); 3.8-4.2 (3H);

Stage 4: 3-[4-(terbutyl dimethyl silyloxy methyl) phenyl]5-methoxymethyl(R)2-oxazolidinone (Code No MD 230247)

130 ml of a toluene solution of 1.93 molar phosgene followed dropwise by 37.8 g (0.252 mol) of diethyl aniline were added to a solution of 43.8 g (0.168 mol) of MD 370488 in 200 ml toluene. After cooling, iced water was added and the organic phase was decanted and dried on $Na_2SO_4$. The solution was then added to a solution of 40 g (0.168 mol) of MD 230246 and 20.5 g (0.168 mol) of dimethyl aminopyridine in 600 ml toluene. After agitation for half an hour, the reaction medium was poured on to water and the organic phase was washed with a solution of sodium bicarbonate and then with saturated NaCl solution. After concentration, the product (84.5 g) was dissolved in 800 ml of ethanol, to which 12.2 g (0.218 mol) of KOH pellets had been added. After agitation for half an hour, the reaction medium was poured on to water and extracted with methylene chloride. The organic phase was dried over $Na_2SO_4$ and concentrated. The expected product was obtained after chromatography [silica, eluent: ethyl acetate (30)/heptane (70)] with a 63% yield:

$[\alpha]^{20}_D$: −46.2° C. (C=1, $CH_3OH$));

IR (KBr) $\nu$ cm$^{-1}$: 1755, 1735;

NMR$^1$H (CDCl$_3$) δ ppm: 0 (6H); 1 (9H); 3.4 (3H); 3.6 (2H); 3.8–4.2 (2H); 4.7 (3H); 7.5 (4H);

M.P.<50° C.

Stage 5: 3-[4-hydroxymethyl phenyl]5-methoxymethyl(R)2-oxazolidinone (Code No. MD 230248)

A solution of 29.2 g (0.083 mol) of MD 230427 and 7.8 g (0.025 mol) of tetrabutyl ammonium fluoride trihydrate in 200 ml THF was agitated at ordinary temperature for 12 hours and the reaction medium was concentrated. The expected product was obtained after chromatography [silica, eluent: ethyl acetate (50)/heptane (50)]:

M.P.=65° C.;

IR (KBr) $\nu$ cm$^{-1}$: 3400, 1750, 1720;

NMR$^1$H (CDCl$_3$) δ ppm: 2.4 (1H exch); 3.35 (3H); 3.6 (2H); 3.8–4.2 (2H); 4.6 (2H); 7.35 (4H).

Stage 6: 3-(4-carboxaldehydo phenyl)5-methoxymethyl(R)2-oxazolidinone (Code No. MD 230 256)

A solution of 12.76 g (0.1630 mol) of DMSO in 80 ml methylene chloride was introduced in 20 minutes into a solution cooled to −60° C. of 12.46 g (0.0982 mol) of oxalyl chloride in 80 ml methylene chloride. 40 minutes later, a solution of 19.6 g (0.0818 mol) of MD 230248 was added in 80 ml methylene chloride followed by 1.4 g (0.409 mol) of triethylamine. After the return to ambient temperature, 300 ml of water was added. The organic phase was washed with water, dried and concentrated. The expected product was obtained after purification by chromatography [silica, eluent: ethyl acetate (70)/heptane (30)] with an 80% yield.

M.P.=96° C.;

$[\alpha]^{20}_D$: −73.4° C. (C=1, $CH_2Cl_2$);

IR (KBr) $\nu$ cm$^{-1}$: 1740, 1690;

NMR$^1$H (CDCl$_3$) δ ppm: 3.4 (3H); 3.7 (2H); 3.8–4.3 (2H); 4.8 (1H); 7.8 (4H); 9.8 (1H).

Stage 7: 3-[4-(4-hydroxy(R)pentyl)phenyl]5-methoxymethyl(R)2-oxazolidinone (Code No. 230238)

A solution of 3.3 g (0.00712 mol) of 2-hydroxy (R) butyltriphenyl phosphonium iodide (Helv. Chim. Acta. 59, 755–757, 1976), 1.34 g (0.00569 mol) of MD 230256 and 2.9 g (0.0213 mol) of $K_2CO_3$ in 10 ml dioxane and 1.5 ml formamide was reflux-heated for 20 hours. After filtration and concentration, the resulting unsaturated product was purified by dissolving it in 30 ml DMF and 0.58 g of imidazole and 0.94 g (0.00625 mol) of terbutyl dimethyl chlorosilane were added. After agitation for 24 hours, the reaction medium was poured on to water. The silylated product was extracted with methylene chloride and purified by chromatography [silica, eluent: ethyl acetate (50)/heptane (50)] with a 36% yield. 0.84 g of the resulting product was dissolved in 15 ml THF in the presence of 0.65 g of tetrabutyl ammonium fluoride for 12 hours. After concentration and purification by chromatography [silica, eluent: ethyl acetate (70)/heptane (30)], 0.53 g (0.0018 mol) of the purified unsaturated product in solution in 10 ml methanol in the presence of 10% palladium on carbon (50% moistened) was hydrogenated at normal pressure. The expected product was obtained with a 55% yield after chromatography [silica, eluent: ethyl acetate (60)/heptane (40)].

$[\alpha]^{20}_D$: −45.8° (C=1, $CH_2Cl_2$);

IR (KBr) $\nu$ cm$^{-1}$: 3400, 1735;

M.P.=47° C.;

NMR$^1$H (CDCl$_3$) δ ppm: 1.2 (3H); 1.5 (4H); 1.8 (1H exch); 2.6 (2H); 3.4 (3H); 3.6 (2H); 3.7–4.2 (3H); 4.7 (1H); 7.2 (2H); 7.4 (2H).

The following were obtained in similar manner: 3-[4-(4-hydroxy(S)pentyl)phenyl]5-methoxymethyl(R)2-oxazolidinone (Code No. MD 230239)

M.P.=53° C.;

$[\alpha]^{20}_D$: −35.9° (C=1, $CH_2Cl_2$);

IR (KBr) $\nu$ cm$^{-1}$: 3400, 1740;

NMR$^1$H (CDCl$_3$) δ ppm: 1.1 (3H); 1.6 (5H, of which 1 exch); 3.4 (3H); 3.6 (2H); 3.7–4.2 (3H); 4.7 (1H); 7.1 (2H); 7.4 (2H)

3-[4-(4-hydroxypentyl)phenyl]5-methoxymethyl(R)2-oxazolidinone (Code No. 230082)

$[\alpha]^{20}_D$: −56.3° (C=1, MeOH);

NMR$^1$H (CDCl$_3$) δ ppm: 1.15 (3H); 1.55 (5H); 2.6 (2H); 3.4 (3H); 3.6 (3H); 3.9 (2H); 4.65 (1H); 7.1 (2H); 7.4 (2H);

IR (microcell) $\nu$ cm$^{-1}$: 3500–3400, 1750.

EXAMPLE 6

3-[4-(5,5,5-trifluoro-4-hydroxypentyl)phenyl]5-methoxymethyl(R)2-oxazolidinone (Code No MD 360207)

Obtained by the method as in Example 5, stage 7, starting from the corresponding raw materials:

Oil;

IR (microcell) $\nu$ cm$^{-1}$: 3410, 1735;

NMR$^1$H (CDCl$_3$) δ ppm: 1 (4H): 2.7 (2H); 3.4 (3H); 3.6 (3H, of which 1 exch); 4 (1H); 4.7 (1H); 7.1 (2H); 7.4 (2H).

EXAMPLE 7

4,4,4-trifluoro 1-iodo 3-butanol (Code No MD 360253)

2.56 g (0.0171 mol) of KI was added to a solution of 2.04 g (0.0068 mol) of MD 370272 (4,4,4-trifluoro 1-tosyloxy 3-butanol) in 20 ml acetone and reflux-heated overnight. After filtration and concentration, the product was obtained by chromatography [silica, eluent: heptane (80)/ethyl acetate (20)]

IR (microcell) $\nu$ cm$^{-1}$: 3400;

NMR$^1$H (CDCl$_3$) δ ppm: 1.9–2.5 (2H); 2.4 (1H exch); 3.35 (2H); 4.2 (1H).

EXAMPLE 8

4,4,4-trifluoro 3-hydroxybutyltriphenylphosphoniumiodide (Code No. MD 360254)

35.6 g (0.14 mol) of MD 360253 and 36.8 g (0.14 mol) of triphenyl phosphine were reflux-heated in dioxane overnight. The product was filtered and dried.
Yield: 72%
M.P.=159° C.

EXAMPLE 9

3-[4-[4,4,4-trifluoro 3-(3-pyridylmethoxy)(R)butoxy]phenyl]5-methoxymethyl(R)2-oxazolidinone (Code No. 360411).

9.6 g (0.03 mol) of compound MD 370503, 9.8 g (0.06 mol) of 3-picolyl chloride, hydrochloride, 0.97 g (0.003 mol) of tetrabutyl ammonium bromide and 14.4 g of 50% NaOH in water were added to 100 ml toluene.

After agitation overnight, the reaction medium was poured on to water. The mixture was acidified with hydrochloric acid. The aqueous phase was washed with toluene, then made alkaline with a solution of sodium carbonate and extracted with ethyl acetate. The organic phase was washed in water, dried on sodium sulphate and concentrated. The expected product was obtained after chromatography on a column [$SiO_2$, eluent: $CH_2Cl_2$ (97)/$CH_3OH$ (3)] with a 45% yield (oil).

IR (microcell) $\nu$ cm$^{-1}$: 1747;
$[\alpha]^{20}_D$: +54.9° (C=1, $CH_2Cl_2$);
NMR$^1$H (CDCl$_3$) δ ppm: 1.8-2.3 (2H); 3.4 (3H); 3.6 (2H); 3.8-4.3 (5H); 4.4-5 (3H); 6.8 (2H); 7-7.6 (4H); 8.5 (2H).

Elementary analysis for $C_{21}H_{23}F_3N_2O_5$:

|  | C | H | N |
|---|---|---|---|
| Calculated (%) | 57.27 | 5.26 | 6.36 |
| Found (%) | 57.14 | 5.27 | 6.26 |

Oxalate of compound MD 360411

A solution of 1.265 g (0.014 mol) of oxalic acid in 30 ml ethyl acetate was added to a solution of 6.190 g (0.014 mol) of the base compound MD 360411 in 20 ml ethyl acetate. The resulting precipitate was filtered and recrystallised from ethyl acetate.
Yield=69%
M.P.=80° C.;
$[\alpha]^{20}_D$: +58.8° (C=1, $CH_2Cl_2$);

Elementary analysis for $C_{23}H_{25}F_3N_2O_9$ + 0.49% $H_2O$:

|  | C | H | N |
|---|---|---|---|
| Calculated (%) | 51.82 | 4.78 | 5.25 |
| Found (%) | 51.77 | 4.59 | 5.38 |

The following were obtained in similar manner but starting from the corresponding substances:

3-[4-[4,4,4-trifluoro 3-(4-pyridylmethoxy)(R)butoxy]phenyl]5-methoxymethyl(R)2-oxazolidinone (Code No MD 290057):
M.P.=91.5° C.
IR (KBr) $\nu$ cm$^{-1}$: 1735
$[\alpha]^{20}_D$: +51.6° (C=1, $CH_2Cl_2$);
NMR$^1$H (CDCl$_3$) δ ppm: 1.8-2.4 (2H); 3.4 (3H); 3.6 (2H); 3.7-4.3 (5H); 4.4-5 (3H); 6.8 (2H); 7.2 (2H); 7.4 (2H); 8.5 (2H);

Elementary analysis for $C_{21}H_{23}F_3N_2O_5$:

|  | C | H | N |
|---|---|---|---|
| Calculated (%) | 57.27 | 5.26 | 6.36 |
| Found (%) | 57.08 | 5.34 | 6.34 |

3-[4-[4,4,4-trifluoro3-(2-pyridylmethoxy)(R)butoxy]phenyl]5-methoxymethyl(R) 2-oxazolidinone (Code No MD 290104):
Liquid:
IR (microcell) $\nu$ cm$^{-1}$: 1750;
$[\alpha]^{20}_D$: +44.7° (C=1, $CH_2Cl_2$);
NMR$^1$H (CDCl$_3$) δ ppm: 1.8-2.4 (2H); 3.4 (3H); 3.6 (2H); 3.75-4.4 (5H); 4.6-5.1 (3H); 6.8 (2H); 7.1 (1H); 7.35 (1H); 7.4 (2H); 7.6 (1H); 8.45 (1H);

Elementary analysis for $C_{21}H_{23}F_3N_2O_5$:

|  | C | H | N |
|---|---|---|---|
| Calculated (%) | 57.27 | 5.26 | 6.36 |
| Found (%) | 57.31 | 5.33 | 6.31 |

Other derivatives (I) and salts were obtained by the methods of operation in Example 9, starting from the compounds obtained in Examples 3, 4 and 5.

EXAMPLE 10

3-[4-[4,4,4-trifluoro3-(3-N-oxide-pyridylmethoxy)(R)butoxy]phenyl]5-methoxymethyl(R) 2-oxazolidinone (Code No MD 290065)

A solution of 4 g (0.0091 mol) of compound MD 360411 in 20 ml methylene chloride was added at 10° C. to a suspension of 3.4 g (0.011 mol) of 55% meta-chloroperbenzoic acid in 40 ml $CH_2Cl_2$. The mixture was then agitated for 24 hours. The reaction medium was made alkaline with 3N ammonia. The aqueous phase was extracted with $CH_2Cl_2$ and the organic phases were washed with water, dried and concentrated. The expected product was obtained after chromatography on a column [$SiO_2$, eluent: $CH_2Cl_2$ (97)/methanol (3)]:
Yield: 84%
$[\alpha]^{20}_D$: +67.1° (C=1, $CH_2Cl_2$);
IR (KBr) $\nu$ cm$^{-1}$: 1475
NMR$^1$H (CDCl$_3$) δ ppm: 1.8-2.3 (2H); 3.4 (3H); 3.6 (2H); 3.7-4.3 (5H); 4.35-4.8 (3H); 6.8 (2H); 7-7.5 (4H); 8 (2H);

Elementary analysis for $C_{21}H_{23}F_3N_2O_6$ + 0.76% $H_2O$:

|  | C | H | N |
|---|---|---|---|
| Calculated (%) | 54.84 | 5.13 | 6.09 |
| Found (%) | 54.64 | 5.21 | 6.19 |

The following are obtained in the same manner, starting from the corresponding raw materials:
3-[4-[4,4,4-trifluoro3-(4-N-oxide-pyridylmethoxy)(R)butoxy]phenyl]5-methoxymethyl(R) 2-oxazolidinone
3-[4-[4,4,4-trifluoro3-(2-N-oxide-pyridylmethoxy)(R)butoxy]phenyl]5-methoxymethyl(R) 2-oxazolidinone

EXAMPLE 11

4,4,4-trifluoro 1-tosyloxy 3-butanol (racemic) and 4,4,4-trifluoro 1-tosyloxy 3-butanol (S)

Obtained by the method in Stage 1 of Example 3 from the diols (racemic and S respectively), which themselves were prepared as per C.A. 111, 31747p from the corresponding acids described in Chimia, Vol. 44, No. 4, pages 90–92, 1990.

The formula (I) derivatives, their N-oxide and their pharmaceutically acceptable salts were studied in laboratory animals and showed pharmocological activity, inter alia in the psychotropic domain, more particularly as potential anti-depressants and anxiolytics.

The anti-depressive activity was shown by the test of potentialisation of 5-HTP in the rat by the method described by M. JALFRE, B. BUCHER, A. COSTON, G. MOCQUET and R. D. PORSOLT: Arch. Int. Pharmacodyn., (1982), 259, 194–221. A determination on the rat was made of that dose of the product which, orally administered, produces generalised tremors or stereotypy (drumming, head movements) in 50% of the animals ($ED_{50}$) after intraperitoneal administration of 5-hydroxy tryptophan (5-HTP) one hour after the first treatment. The results obtained in the preceding test, using some compounds according to the invention, are given by way of example in the following table:

| Compound tested Code number | $ED_{50}$ mg/kg/p.o. |
|---|---|
| MD 360411 (oxalate) | 0.4 |
| MD 290057 | 0.53 |
| MD 290065 | 0.62 |

The compounds according to the invention have a therapeutic index such that they can be safely used at the active doses.

As the preceding results show, the compounds according to the invention [derivatives (I), their N-oxide and pharmaceutically acceptable salts] can be used in the preparation of psychotropic drugs, inter alia potential anti-depressants and anxiolytics, the drugs being of use in therapy, inter alia for treatment of endogenic and exogenic depressive states.

The drugs can be administered to man or any warm-blooded animal in various pharmaceutical forms well known in the art, inter alia in the form of compounds formulated for oral, injectable or rectal administration.

For oral administration, the compositions can be in the form of compressed tablets, dragees or capsules prepared by conventional means using known supports and excipients such as binders, fillers, lubricants or disintegration agents; alternatively they may be in the form of solutions, syrups or suspensions.

For administration in the form of injectable solutes, the compositions according to the invention can be in the form of injectable solutions, suspensions or emulsions comprising an acceptable oily or aqueous liquid vehicle.

For rectal administration, the compounds can be in the form of a suppository comprising the conventional bases for suppositories.

The active therapeutic dose of the active principles, i.e. of derivatives (I), their pharmaceutically acceptable salts and N-oxide, depends inter alia on the method of administration, the body weight of the patient and the therapeutic power of the active principles used.

Orally administered doses may generally be up to 10 mg/kg per day of active principle (in one or two doses); the injectable amounts are up to 1 mg/kg per day (in one or more doses) and the rectal amounts can be up to 5 mg/kg per day of active principle (in one or more suppositories).

We claim:

1. Oxazolidinone compounds of the formula:

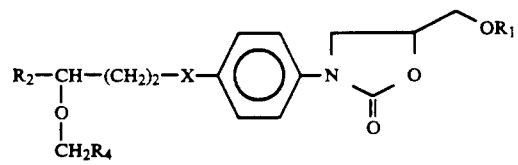

wherein $R_1$ is $C_1$–$C_4$ alkyl; X is an oxygen atom or a methylene group; $R_2$ is $C_1$–$C_4$ alkyl or $CF_3$; and $R_4$ is a pyridyl group selected from 2-pyridyl, 3-pyridyl or 4-pyridyl;

and their N-oxide forms and the acid addition salts of the compounds and their N-oxide forms, the compounds being in various stereoisomeric forms or in the form of a mixture of these forms, including the racemic form.

2. The oxazolidinone compounds of claim 1, in which $R_2$ is $CF_3$.

3. The oxazolidinone compounds of claim 2, wherein the asymmetrical carbon in the oxazolidinone ring has the configuration (R).

4. The oxazolidinone compounds of claim 2, wherein the asymmetrical carbon of the group $R_2$—$C^*$—$H(OCH_2R_4)$— has the configuration (R).

5. The oxazolidinone compounds of claim 2, wherein the asymmetrical carbon of the group $R_2$—$C^*$—$H(OCH_2R_4)$— has the configuration (S).

6. The oxazolidinone compounds of claim 2, wherein the configuration is (R, R).

7. The oxazolidinone compounds of claim 2, in the form of acid addition salts.

8. The oxazolidinone compounds of claim 3, in the form of acid addition salts.

9. The oxazolidinone compounds of claim 4, in the form of acid addition salts.

10. The oxazolidinone compounds of claim 5, in the form of acid addition salts.

11. The oxazolidinone compounds of claim 6, in the form of acid addition salts.

12. The oxazolidinone compounds of claim 1, selected from the group consisting of compounds having the formula:

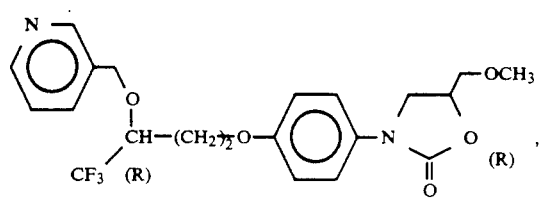

-continued

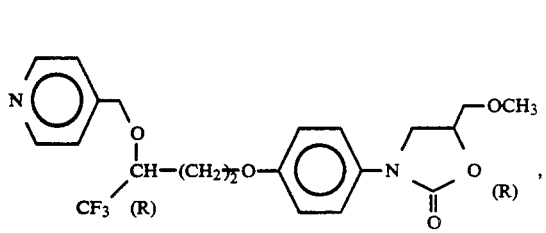

and

-continued

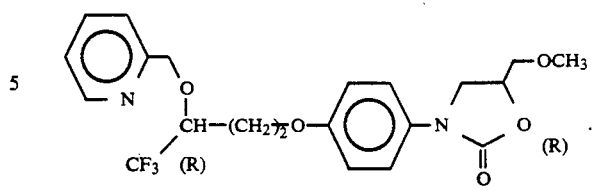

13. The oxazolidinone compounds of claim 12 in the N-oxide form.

14. A pharmaceutical composition comprising a pharmaceutically effective amount of a compound of claim 1 and a pharmaceutically acceptable carrier.

15. A method for treating a patient in need of a psychotropic drug comprising administering to said patient the pharmaceutical composition of claim 14.

* * * * *